United States Patent
Decampo et al.

(10) Patent No.: US 9,745,239 B2
(45) Date of Patent: Aug. 29, 2017

(54) CYCLOALKANE OXIDATION CATALYSTS AND METHOD TO PRODUCE ALCOHOLS AND KETONES

(71) Applicants: RHODIA OPERATIONS, Paris (FR); ECOLE NORMALE SUPERIEURE DE LYON, Lyons (FR)

(72) Inventors: Floryan Decampo, Pittsburgh, PA (US); Wenjuan Zhou, Shanghai (CN)

(73) Assignees: Rhodia Operations, Paris (FR); Ecole Normale Supericure De Lyon, Lyons (FR)

( * ) Notice: Subject to any disclaimer, the term of this patent is extended or adjusted under 35 U.S.C. 154(b) by 0 days.

(21) Appl. No.: 14/784,845

(22) PCT Filed: Apr. 17, 2014

(86) PCT No.: PCT/EP2014/057855
§ 371 (c)(1),
(2) Date: Oct. 15, 2015

(87) PCT Pub. No.: WO2014/170422
PCT Pub. Date: Oct. 23, 2014

(65) Prior Publication Data
US 2016/0060199 A1 Mar. 3, 2016

(30) Foreign Application Priority Data
Apr. 18, 2013 (WO) ............... PCT/CN2013/074348

(51) Int. Cl.
*C07C 45/28* (2006.01)
*C07C 29/48* (2006.01)

(52) U.S. Cl.
CPC ............. *C07C 45/28* (2013.01); *C07C 29/48* (2013.01); *C07C 2101/08* (2013.01); *C07C 2101/14* (2013.01); *C07C 2101/18* (2013.01)

(58) Field of Classification Search
CPC ................................. C07C 45/28; C07C 29/48
See application file for complete search history.

(56) References Cited

U.S. PATENT DOCUMENTS

| 4,918,238 A * | 4/1990 | Costantini | ............... C07C 29/48 568/311 |
| 2009/0131724 A1* | 5/2009 | Corma | ................... C07C 29/50 568/360 |

OTHER PUBLICATIONS

Kobayashi et al. ("Highproduction of adamantine oxygenates in propionic acid using VO(acac)2 and Eu(OTf)3 with O2" Journal of Molecular Catalysis A: Chemcial, 294, (2008), 43-50).*
Ruiter et al. ("The system iron(II)mpzbpy mediate the H2O2 oxidation of cyclohexane and cyclooctane and the aerobic oxidative cleavage of ascorbic acid to oxalate" Inorganic Chemistry Communications, 11, (2008), 787-790).*

* cited by examiner

*Primary Examiner* — Peter F Godenschwager
(74) *Attorney, Agent, or Firm* — Osha Liang LLP

(57) ABSTRACT

The present invention concerns a method of oxidizing a cycloalkane to form a product mixture containing a corresponding alcohol and ketone, said method comprising contacting a cycloalkane with an oxidant agent in the presence of catalytic effective amount of metal triflates or metal triflimidates catalysts.

9 Claims, No Drawings

CYCLOALKANE OXIDATION CATALYSTS AND METHOD TO PRODUCE ALCOHOLS AND KETONES

The present application is a U.S. national stage entry under 35 U.S.C. §371 of International Application No. PCT/EP2014/057855, filed Apr. 17, 2014, which claims priority to international application No. PCT/CN2013/074348, filed on Apr. 18, 2013, the content of each of these applications is incorporated herein by reference for all purposes.

The present invention concerns a method of oxidizing a cycloalkane to form a product mixture containing a corresponding alcohol and ketone, said method comprising contacting a cycloalkane with an oxidant agent in the presence of catalytic effective amount of metal triflates or metal triflmidates catalysts.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Several different processes have been used for the oxidation of cyclohexane into a product mixture containing cyclohexanone and cyclohexanol. Such product mixture is commonly referred to as a KA (ketone/alcohol) mixture. The KA mixture can be readily oxidized to produce adipic acid, which is an important reactant in processes for preparing certain condensation polymers, notably polyamides. Given the large quantities of adipic acid consumed in these and other processes, there is a need for cost-effective processes for producing adipic acid and its precursors.

Classical process to produce a mixture containing cyclohexanone and cyclohexanol is conducted in two steps to get KA oil through oxidation of cyclohexane. First, the thermal auto-oxidation of cyclohexane leads to the formation of cyclohexyl hydroperoxide (HPOCH) that is isolated. The second step, KA oil is obtained through the decomposition of HPOCH which is catalyzed by using chromium ions or cobalt ions as homogenous catalysts.

With the regulation restrictions all over the world, the requirement of replacement of environmentally unfriendly catalysts, such as chromium catalysts, becomes more and more urgent. The environmental footprint and the economics of this process could be significantly improved if the current homogeneous catalysts could be replaced by non-toxic catalysts.

Various types of homogeneous catalysts have been used to catalyze oxidation of cyclohexane and decomposition of cyclohexyl hydroperoxide to produce KA oil.

As example, U.S. Pat. No. 3,923,895 describes a process of decomposition of cyclohexyl hydroperoxide with soluble chromium derivatives in the presence of the phosphate ester at 80° C.-150° C. Also, U.S. Pat. No. 4,465,861 discloses a process of decomposing cyclohexyl hydroperoxide using in the decomposition step a catalyst composition consisting essentially of (a) a specified salt of chromium, cobalt, iron, manganese, molybdenum or vanadium and (b) as a stabilizing agent, an alkylsulfonic acid, an alkylarenesulfonic acid, an alkylammonium sulfonate, or an alkylphosphonium sulfonate. EP 0230254 B1 reports decomposition of cyclohexyl hydroperoxide with cobalt salt in the presence of phosphonic acid derivatives. EP 0768292 B1 reports the process of decomposition of cyclohexyl hydroperoxide with Co or Cr in the presence of an alkali metal hydroxide and one or more alkali metal salts in aqueous phase. The alkali metal salts are preferably metal alkali carbonates or alkali metal salts of mono- and poly-carboxylic acids. U.S. Pat. No. 4,918,238 reports osmium tetroxide as the catalyst on the decomposition of cyclohexyl hydroperoxide. The process of decomposition of cyclohexyl hydroperoxide with cobalt catalyst in alkaline solution is disclosed in US 20030229253A1. U.S. Pat. No. 7,632,942 reports the oxidation of cyclohexane by oxygen in the presence of cobalt salt of carboxylic acid and cobalt complex with porphyrin as a ligand.

Moreover, Hansen et al (Journal of molecular catalysis A: Chemical, 1995, 102, 117-128) uses ruthenium tetraarylporphyrins as catalysts in the decomposition of cyclohexyl hydroperoxide.

There remains a need of catalyst with high oxidation ability to get high conversion of cyclohexane and high selectivity to KA oil in relatively low cycloalkyl hydroperoxide concentration with low cost of catalyst preparation.

INVENTION

It appears now that it's perfectly possible to produce a mixture of alcohol and ketone from a cycloalkane with a high oxidation ability, high selectivity to KA oil with a good compromise of conversion and yield. Such results can be obtained with the use of a catalytic effective amount of metal triflates or metal triflmidates catalysts that showed a high oxidation ability with a relatively low oxidant level.

The present invention then concerns a method of oxidizing a cycloalkane to form a product mixture containing a corresponding alcohol and ketone, said method comprising contacting a cycloalkane with an oxidant agent in the presence of at least a catalyst of formula (I) as follow:

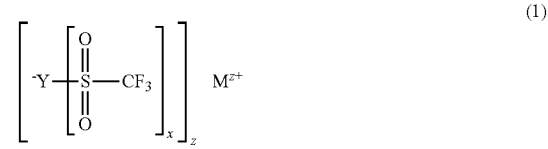

wherein:
Y is N or O;
X=1 when Y=O or 2 when Y=N;
Z is valency of the metal, preferably comprised between 1 and 4; and
M is a metal chosen in the group consisting of: transition metal, post transition metal, and lanthanide; valency of M depends on Z.

Valency, also known as valence or valence number, is the number of valence bonds a given atom has formed, or can form, with one or more other atoms.

Other characteristics, details and advantages of the invention will emerge even more fully upon reading the description which follows.

Throughout the description, including the claims, the term "comprising one" should be understood as being synonymous with the term "comprising at least one", unless otherwise specified, and "between" should be understood as being inclusive of the limits.

Cycloalkane

Cycloalkane may refer to saturated cyclic hydrocarbons having from 3 to about 10 carbon atoms, more usually from about 5 to about 8 carbon atoms. Non-limiting examples of cycloalkanes include cyclopentane, cyclohexane, cycloheptane, and cyclooctane.

Oxidant Agent

Oxydant agents according to the present invention may be for example air, $O_2$ or hydroperoxide.

Specific examples of the hydroperoxide compounds which are usable in the present may be represented by the formula (II) as follows:

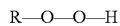  (II)

wherein R is a hydrocarbon group that may comprise from 3 to 15 carbon atoms, mainly alkyl or aryl groups.

As used herein, the term "hydrocarbon group" refers to a group consisting of carbon atoms and hydrogen atoms, which group may be saturated or unsaturated, linear, branched or cyclic, aliphatic or aromatic. Hydrocarbon groups of the present invention may be alkyl groups, alkenyl groups, or aryl groups.

Alkyl as used herein means a straight chain or branched saturated aliphatic hydrocarbon. As used herein, unless stated otherwise, the term "alkyl" means a linear or branched alkyl group optionally substituted with one or more substituent selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

Aryl as used herein means a 6-carbon monocyclic or 10-carbon bicyclic aromatic ring system wherein 0, 1, 2, 3, or 4 atoms of each ring are substituted by a substituent, such as O or N. Examples of aryl groups include phenyl, naphthyl and the like.

Hydroperoxides are preferably chosen in the group consisting of: tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin (i.e., tetrahydronaphtalene) hydroperoxide, isobutylbenzene hydroperoxide, and ethylnaphthalene hydroperoxide.

More preferably hydroperoxides are alkyl hydroperoxides such as tert-butyl hydroperoxide or cyclohexyl hydroperoxide.

These hydroperoxides may also be used in combination of two or more species thereof.

The hydroperoxides concerned with the invention may be generated in situ, notably by reaction of a cycloalkane with oxygen or an oxygen generator, or added to the reaction medium, notably at the start or during the reaction.

The reaction medium may comprise a cycloalkane and 2 to 40 wt. % of oxidant agent according to the total weight of the reaction, more preferably 5 to 20 wt. % of oxidant agents. In an embodiment of the present invention, the reaction medium comprises a cycloalkane and 2 to 40 wt. % of hydroperoxides according to the total weight of the reaction, more preferably 5 to 20 wt. % of hydroperoxides.

Catalyst of Formula (I)

Metal triflates catalysts of formula (I) are obtained when Y is an oxygen atom.

Metal triflimidates are obtained when Y is a nitrogen atom.

Metal according to the present invention may be chosen in the group consisting of:
transition metal, such as for example Fe, Y, Cu and Cr,
post transition metal, such as for example Bi and In,
lanthanide, such as for example Nd and Ce.

M is then preferably chosen in the group consisting of: Fe, Y, Cu, Cr, Bi, In, Nd and Ce.

Catalysts of the present invention are preferably chosen in the group consisting of: $Fe(OTf)_3$, $Cu(OTf)_2$, $Y(OTf)_3$, $Fe(TSIF)_3$, $Cu(TFSI)_2$, $Ce(TFSI)_3$, $In(TFSI)_3$ and $Bi(TFSI)_3$.

Catalyst of the present invention may be used in a range comprised between 0.0001 wt. % to 10 wt. %, preferably between 0.001 wt. % and 0.1 wt. %, in relation of metal weight to the total weight of the reaction medium.

A combination of two or more catalysts may be used during the reaction of the present invention, notably in blend.

Catalyst of the invention may be used in a homogeneous or heterogeneous way.

Catalyst may be supported on a carrier, such as for example one of the oxides, carbons or organic or inorganic resins. Notably, the carrier may be selected from the group consisting of silica, alumina, zirconia, titania, ceria, magnesia, lanthania, niobia, yttria, zeolite, perovskite, silica clay, and iron oxide and mixtures thereof. The catalyst may be supported on a carrier in any convenient fashion, particularly by adsorption, ion-exchange, grafting, trapping, impregnation, or sublimation.

Parameters of the Reaction

In the practice of the invention, the catalysts can be contacted with a cycloalkane, such as cyclohexane, by formulation into a catalyst bed, which is arranged to provide intimate contact between the catalyst and reactants. Alternatively, catalysts can be slurried with reaction mixtures using techniques known in the art. The process of the invention is suitable for either batch or continuous cycloalkane oxidation. These processes can be performed under a wide variety of conditions, as will be apparent to persons of ordinary skill.

Suitable reaction temperatures for the process of the invention typically range from about 20 to about 200° C., preferably from about 40 to about 140° C.

Reaction pressures often range from about 0.1 MPa (1 bar) to about 20 MPa (200 bar), such values not being absolutely critical. Cycloalkane reactor residence time generally varies in inverse relation to reaction temperature, and typically is comprised between 30 and 1440 minutes. Pure oxygen, air, oxygen-enriched or oxygen-depleted air or, alternatively, oxygen diluted with an inert gas, can be used in the reaction medium.

A solvent may be eventually employed in the reaction medium. Preferably solvents are chosen in the group of a polar protic or a polar aprotic solvent, preferably acetonitrile or acetic acid.

Suitable polar aprotic solvents may be for instance chosen in the group consisting of: tetrahydrofuran, acetone, acetonitrile, and DMSO.

Suitable polar protic solvents may be for instance chosen in the group consisting of: acetic acid, formic acid, isopropanol, ethanol, and methanol.

One or several solvent(s) may be used in combination in the reaction medium.

The catalysts of the present invention may be recovered and regenerated or reproduced. More specifically, the catalyst may be regenerated so that it has an initial activity, for example, by recovering and drying the catalyst.

At the end of the reaction, the compound of interest may be eventually purified by well known methods of the technical field, such as distillation.

Should the disclosure of any of the patents, patent applications, and publications which are incorporated herein by reference conflict with the description of the present application to the extent that it may render a term unclear, the present description shall take precedence.

The following examples are provided for illustrative purposes only and should not be regarded as limiting the invention.

EXPERIMENTAL PART

Example 1

Several catalysts have been used to catalyze the oxidation of cyclohexane using t-butyl hydroperoxide (TBHP) at 80° C. for 1.0 h with 0.02 g catalyst and 7.7 wt. % TBHP in cyclohexane. Molar ratio TBHP/catalyst is 79.3. Results are mentioned in Table 1.

TABLE 1

| Trials | Catalyst | TBHP Conversion (%) | KA Selectivity (%) | KA Yield (%) |
|---|---|---|---|---|
| C1 | None | 0.7 | 98.0 | 0.7 |
| C2 | Co(NO$_3$)$_2$ | 49 | 44 | — |
| C3 | Triflic acid | 99.7 | 4.2 | 4.2 |
| 1 | Fe(OTf)$_3$ | 100 | 30.2 | 30.2 |
| 2 | Cu(OTf)$_2$ | 75 | 30.0 | 22.5 |
| 3 | Y(OTf)$_3$ | 55.8 | 27.2 | 15.2 |
| 4 | Fe(TSIF)$_3$ | 100 | 23.1 | 23.1 |
| 5 | Cu(TFSI)$_2$ | 84.7 | 29.8 | 25.2 |
| 6 | Ce(TFSI)$_3$ | 72.4 | 14.1 | 10.2 |
| 7 | In(TFSI)$_3$ | 81.6 | 12.6 | 10.3 |
| 8 | Bi(TFSI)$_3$ | 91.3 | 11.8 | 10.8 |

Trial C2 is using Co(NO$_3$)$_2$ catalyst as mentioned in EP 0768292 A1.

It appears then that without any catalysts, TBHP conversion and KA yield are less than 1%, while with the catalysts of the present invention a high conversion of TBHP with important KA yields and KA selectivities can be obtained.

The invention claimed is:

1. A method of oxidizing a cycloalkane to form a product mixture containing a corresponding alcohol and ketone, comprising contacting a cycloalkane with an oxidant agent in the presence of at least a catalyst of formula (I) as follow:

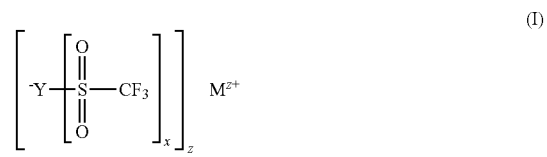

wherein:
Y is N or O;
X=1 when Y=O or 2 when Y=N;
M is a metal selected from the group consisting of transition metal, post transition metal, and lanthanide; and
Z is valency of the metal M; and
wherein the oxidant agent is a hydroperoxide compound corresponding to formula (II):

R—O—O—H  (II)

wherein R is a hydrocarbon group comprising from 3 to 15 carbon atoms.

2. A method according to claim 1, wherein cycloalkane is selected from the group consisting of cyclopentane, cyclohexane, cycloheptane, and cyclooctane.

3. A method according to claim 1, wherein hydroperoxide compounds are selected from the group consisting of tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin hydroperoxide, isobutylbenzene hydroperoxide, and ethylnaphthalene hydroperoxide.

4. A method according to claim 1, wherein Y is an oxygen atom.

5. A method according to claim 1, wherein Y is a nitrogen atom.

6. A method according to claim 1, wherein M is selected from the group consisting of Fe, Y, Cu, Cr, Bi, In, Nd, and Ce.

7. A method according to claim 1, wherein the at least one catalyst of formula (I) is selected from the group consisting of Fe(OTf)$_3$, Cu(OTf)$_2$, Y(OTf)$_3$, Fe(TSIF)$_3$, Cu(TFSI)$_2$, Ce(TFSI)$_3$, In(TFSI)$_3$, and Bi(TFSI)$_3$.

8. A method according to claim 1, wherein at least one catalyst of formula (I) is used in a range of between 0.0001 wt % to 10 wt. %, in relation of metal weight to the total weight of the reaction medium.

9. A method according to claim 1, wherein the cycloalkane is contacted with an oxidant agent in the presence of at least a catalyst of formula (I) in a reaction medium that comprises a polar aprotic or a polar protic solvent.

* * * * *